United States Patent [19]

Fürst et al.

[11] 4,140,700
[45] Feb. 20, 1979

[54] D-HOMOPREGNANES

[75] Inventors: Andor Fürst, Basel; Peter Keller, Reinach; Marcel Müller, Frankendorf, all of Switzerland

[73] Assignee: Hoffmann-La Roche Inc., Nutley, N.J.

[21] Appl. No.: 861,465

[22] Filed: Dec. 16, 1977

[30] Foreign Application Priority Data

Dec. 20, 1976 [AT] Austria .................................. 9445/76

[51] Int. Cl.$^2$ ...................... C07C 61/38; C07D 307/94
[52] U.S. Cl. .................................. 260/343.6; 562/498; 424/279; 424/317
[58] Field of Search ................... 560/116; 260/514 G, 260/343.6

[56] References Cited
U.S. PATENT DOCUMENTS 3,415,845  10/1968  Knox ................................. 260/340.5

Primary Examiner—Robert Gerstl
Attorney, Agent, or Firm—Jon S. Saxe; George M. Gould; Raymond R. Wittekind

[57] ABSTRACT

D-Homopregnanes of the formula

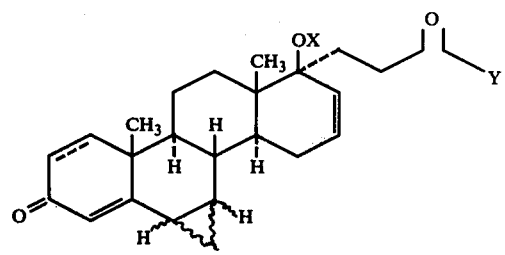

wherein X is hydrogen, Y is hydroxy or X and Y taken together denote an oxygen to carbon bond and the dotted line in the 1,2-position of the A-ring together with the corresponding solid line denotes a single or double carbon-to-carbon bond or a pharmaceutically acceptable basic addition salt thereof when Y is hydroxy having diuretic activity are disclosed.

6 Claims, No Drawings

D-HOMOPREGNANES

DESCRIPTION OF THE INVENTION

The present invention relates to D-homosteroids. More particularly, the invention is concerned with D-homopregnanes, a process for the preparation thereof and pharmaceutical preparations containing same.

The D-homosteroids provided by the present invention are compounds of the general formula

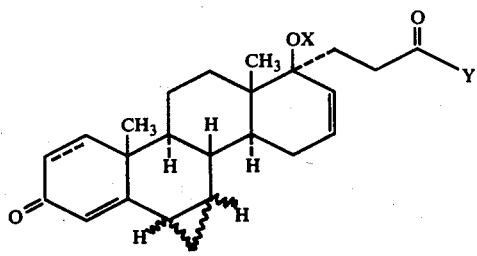

I wherein X is hydrogen, Y is hydroxy or X and Y taken together denote an oxygen to carbon bond and the dotted line in the 1,2-position of the A-ring together with the corresponding solid line denotes a single or double carbon-to-carbon bond or a pharmaceutically acceptable basic addition salt thereof when Y is hydroxy.

In the formulae presented herein, the various substituents are joined to the cyclic nucleus by one of three notions: a solid line (—), indicating a substituent which is in the β-orientation (above the plane of the paper), a dotted line (--), indicating a substituent which is in the β-orientation (below the plane of the paper), or a wavy line (∿), indicating a substituent which may either be in the α- or β-orientation. The position of the methyl groups in the 10- and 13-positions have been arbitrarily indicated as the β-orientation which is consistent with the absolute stereochemistry of the products described in the examples. It is to be understood, however, that in the formulae presented both in the specification and in the appended claims, there is intended to be represented both of the enantiomeric series, as well as mixtures thereof, such as enantiomeric mixtures.

Of particular interest are the compounds of formula I in which X is hydrogen and Y is hydroxy and pharmaceutically acceptable basic addition salts thereof, especially alkali metal salts, e.g., potassium and sodium salts, ammonium salts and alkaline earth metal salts, e.g., calcium salts. Potassium salts are preferred.

Also preferred are the 1,2-saturated compounds of formula I, the 6β,7β-compounds of formula I and the pharmaceutically acceptable basic addition salts thereof, e.g., 17a-hydroxy-6β,7β-methylene-3-oxo-D-homo-17aα-pregna-4,16-diene-21-carboxylic acid and its potassium salt.

Examples of other compounds of formula I are:
6β,7β-methylene-3-oxo-D-homo-17aα-pregna-4,16-diene-21,17a-carbolactone and
6α,7α-methylene-3-oxo-D-homo-17aα-pregna-4,16-diene-21,17a-carbolactone.

According to the process provided by the present invention, the D-homosteroids, i.e., the compounds of formula I and the pharmaceutically acceptable basic addition salts thereof, are prepared by methylenating a D-homosteroid of the general formula

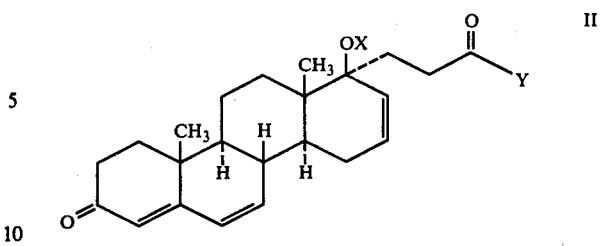

II wherein X and Y are as above or a pharmaceutically acceptable basic addition salt thereof in the 6,7-position and, if desired, in an optional sequence, dehydrogenating the resulting compound of formula I or a pharmaceutically acceptable basic addition salt thereof in the 1,2-position, by cleaving the lactone ring in a compound of formula I in which X and Y taken together denote an oxygen to carbon bond and isolating the product in the form of the free acid or a pharmaceutically acceptable basic addition salt thereof or by lactonizing a compound of formula I in which X is hydrogen and Y is hydroxy or a pharmaceutically acceptable basic addition salt thereof.

The methylenation of a D-homosteroid of formula II or of a pharmaceutically acceptable basic addition salt of a compound of formula II in which X is hydrogen and Y is hydroxy, e.g., an alkali metal, ammonium or alkaline earth metal salt, can be carried out in a known method, for example, by means of trimethylsulfoxonium iodide in the presence of a base such as sodium hydride or potassium tert. butylate in an aprotic dipolar solvent, e.g., dimethylsulfoxide, tetrahydrofuran, hexamethylphosphoric acid triamide, dimethylformamide or mixtures thereof at a temperature between about 0° C. and 50° C., suitably at room temperature.

The 1,2-dehydrogenation of a compound of formula I or of a pharmaceutically acceptable basic addition salt thereof can be carried out by known methods, for example, by microbiological methods or by means of dehydrogenating agents such as selenium dioxide, 2,3-dichloro-5,6-dicyanobenzoquinone, chloranil, thallium triacetate or lead tetraacetate. Suitable microorganisms for the 1,2-dehydrogenation are, for example, Schizomycetes, especially those of the genera Arthrobacter, e.g., A. simplex ATCC 6946, Bacillus, e.g., B. lentus ATCC 13805 and B. sphaericus ATCC 7055, Pseudomonas, e.g., P. aeruginosa IFO 3505, Flavobacterium, e.g., F. flavescens IFO 3058, Lactobacillus, e.g., L. brevis IFO 3345, and Nocardia, e.g., N. Opaca ATCC 4276.

The cleavage of the lactone ring of a compound of formula I can be carried out by known methods, for example, by means of a base such as potassium hydroxide or sodium hydroxide in a solvent, e.g., an alcohol such as methanol, ethanol or isopropanol, at a temperature between about 0° C. and the reflux temperature of the mixture, conveniently at about 50° C. The resulting salts, which correspond to the bases used, can be converted by acidification, e.g., by means of hydrochloric acid, into the free acids of formula I. The latter can be converted into pharmaceutically acceptable basic addition salts by treatment with suitable bases.

The lactonization of a compound of formula I in which X is hydrogen and Y is hydroxy or of a pharmaceutically acceptable basic addition salt thereof can be carried out by known methods, for example, by means of a strong acid such as hydrochloric acid, sulfuric acid or p-toluenesulfonic acid in a solvent, e.g., water, an alcohol such as methanol, or mixtures thereof, at a temperature between about −50° C. and 100° C., suitably at room temperature.

The starting materials of formula II in which X is hydrogen and Y is hydroxy and pharmaceutically acceptable basic addition salts thereof can be prepared by cleaving the lactone ring of compounds of formula II wherein X and Y taken together denote an oxygen to carbon bond, the cleavage being carried out in the same manner as described earlier in connection with the cleavage of the lactone ring of a compound of formula I wherein X and Y taken together denote an oxygen to carbon bond.

The D-homosteroids of the present invention exhibit pharmacological activity. Inter alia, they show diuretic activity and are suitable for blocking the action of aldosterone or desoxycorticosterone acetate. Accordingly, they can be used, for example, as potassium-sparing diuretics or for the flushing of edemas. They may be administered, for example, in a dosage of from about 0.1 mg/kg to 10 mg/kg per day.

The D-homosteroids of the present invention show advantages over known compounds having aldosterone antagonistic activity, especially in relation to side-effects. Thus, it has been shown that potassium 17a-hydroxy-6$\beta$,7$\beta$-methylene-3-oxo-D-homo-17a$\alpha$-pregna-4,16-diene-21-carboxylate has a comparable aldosterone antagonistic activity to the known spironolactone, 7$\alpha$-acetylthio-3-oxo-17$\alpha$-pregn-4-ene-17,21-carbolactone, but has substantially less antiandrogenic and gestagenic side-effects.

The D-homosteroids provided by the present invention can be used as medicaments, for example, in the form of pharmaceutical preparations which contain them in association with a compatible pharmaceutical carrier material. This carrier material can be an organic or inorganic inert carrier material suitable for enteral or parenteral administration such as, for example, water, gelatin, gum arabic, lactose, starch, magnesium stearate, talc, vegetable oils, polyalkyleneglycols, petroleum jelly, etc. The pharmaceutical preparations can be made up in a solid form, e.g., as tablets, dragees, suppositories, or capsules, or in a liquid form, e.g., as solutions, suspensions or emulsions. The pharmaceutical preparations may be sterilized and/or may contain adjuvants such as preserving, stabilizing, wetting or emulsifying agents, salts for varying the osmotic pressure or buffers. They can also contain other therapeutically valuable substances.

The pharmaceutical preparations can be prepared by known methods, e.g., by mixing a compound of formula I or a pharmaceutically acceptable basic addition salt thereof with non-toxic, inert, solid and/or liquid carrier materials which are customary in such preparations and which are suitable for therapeutic administration, e.g., carrier materials previously named, and, if desired, bringing the mixture into the desired dosage form.

The following examples illustrate the process provided by the present invention.

EXAMPLE 1

Trimethylsulfoxonium iodide (96.64 g.) was dry-mixed in a nitrogen atmosphere with 18.2 g. of a 55% sodium hydride dispersion. Subsequently, with cooling to 15°–17° C., 300 ml. of dimethylsulfoxide was added dropwise over 10 minutes. After completion of hydrogen evolution, the suspension was stirred under nitrogen at room temperature for 3.5 hours. 3-Oxo-D-homo-17a$\alpha$-pregna-4,6,16-triene-21,17a-carbolactone (77.4 g.) dissolved in 500 ml. of dimethylsulfoxide was added dropwise at room temperature over 15 minutes. The brown-red solution was stirred at room temperature under nitrogen for 113 hours. For workup, the mixture containing sodium 17a-hydroxy-6$\beta$,7$\beta$-methylene-3-oxo-D-homo-17a$\alpha$-pregna-4,16-diene-21-carboxylate was acidified with 100 ml. of glacial acetic acid, poured into water and extracted with methylene chloride. The crude product was dissolved in 200 ml. of methanol. 1N Hydrochloric acid (10 ml.) was added. After stirring at room temperature for 1 hour, the solution was neutralized with sodium bicarbonate, concentrated on a rotary evaporator, poured into water and extracted with methylene chloride. Chromatography on silica gel using ether for elution and subsequent crystallization from acetone/hexane gave 15 g. of 6$\beta$,7$\beta$-methylene-3-oxo-D-homo-17a$\alpha$-pregna-4,16-diene-21,17a-carbolactone, m.p. 226°–229° C.; UV $\lambda_{max}$ 265 nm, $\epsilon$ = 19000, $[\alpha]_D$ = −210° (c = 0.101, methanol) and 15 g. of 6$\alpha$,7$\alpha$-methylene-3-oxo-D-homo-17a$\alpha$-pregna-4,16-diene-21,17a-carbolactone, m.p. 231°–233° C.; UV $\lambda_{max}$ 257.5 nm, $\epsilon$ = 17300, $[\alpha]_D$ = +82° (c = 0.102, methanol).

The above methylenation can be carried out using, in place of sodium hydride as the base and dimethylsulfoxide as the solvent, sodium hydride and dimethylsulfoxide/tetrahydrofuran or potassium tert. butylate and dimethylformamide, hexamethylphosphoric acid triamide or dimethylsulfoxide.

EXAMPLE 2

Trimethylsulfoxonium iodide (169.2 g.) and 31.95 g. of a 55% sodium hydride dispersion was dry-mixed in an argon atmosphere. With cooling to 15° C., 693 ml. of dimethylsulfoxide was slowly added. The resulting suspension was stirred at room temperature for 3.5 hours. A solution of 58 g. of potassium 17a-hydroxy-3-oxo-D-homo-17a$\alpha$-pregna-4,6,16-triene-21-carboxylate in 462 ml. of dimethylsulfoxide was then added dropwise with cooling to room temperature. After 24 hours, there was added with cooling 162 ml. of acetic acid and the mixture was poured into water. The precipitate was filtered and washed with a small amount of water. The residue was dissolved in ethanol, evaporated and dried. The crude product was dissolved in 273 ml. of methanol, acidified with 6 ml. of 1N hydrochloric acid and kept at room temperature for 60 minutes. The solution was poured into water and extracted with ethyl acetate. The crude product was chromatographed on silica gel with hexane/ether (1:1) and ether. After crystallization from acetate/hexane, there was obtained 13 g. of 6$\beta$,7$\beta$-methylene-3-oxo-D-homo-17a$\alpha$-pregna-4,16-diene-21,17a-carbolactone and 10 g. of 6$\alpha$,7$\alpha$-methylene-3-oxo-D-homo-17a$\alpha$-pregna-4,16-diene-21,17a-carbolactone.

The foregoing methylenation can be carried out using, in place of sodium hydride as the base and dimethylsulfoxide as the solvent, sodium hydride and dimethylsulfoxide/tetrahydrofuran or potassium tert. butylate and dimethylformamide, hexamethylphosphoric acid triamide or dimethylsulfoxide.

The starting material can be prepared as follows:
3-Oxo-D-homo-17a$\alpha$-pregna-4,6,16-triene-21,17a-carbolactone (50g) was suspended in 750 ml of isopropanol and 55.7 ml of aqueous 2.49N potassium hydroxide solution are added. The suspension was boiled at reflux under argon for 40 minutes, a solution being obtained. The solution was concentrated with repeated addition of isopropanol. There was obtained potassium 17a-hydroxy-3-oxo-D-homo-17aα-pregna-4,6,16-triene-21-carboxylate which, after crystallization from ethanol/ethyl acetate, had mp 210°–215° C. (with decomposition); UV $\lambda_{max}$ = 256 nm, $\epsilon$ = 12480.

EXAMPLE 3

6β,7β-Methylene-3-oxo-D-homo-17aα-pregna-4,16-diene-21,17a-carbolactone (60.6g) was suspended in 745 ml of isopropanol and 69.55 ml of 2.33N potassium hydroxide solution and boiled at reflux under argon for 40 minutes. The solution was gradually cooled to +5° C., the potassium salt crystallizing out. The precipitate was filtered, washed with 100 ml of cold isopropanol and dried in vacuo. There was obtained 47 g of potassium 17a-hydroxy-6β,7β-methylene-3-oxo-D-homo-17aα-pregna-4,16-diene-21-carboxylate, mp 254°–256° C. (with decomposition); UV $\lambda_{max}$ = 267 nm, $\epsilon$ = 17000.

EXAMPLE 4

Potassium 17a-hydroxy-6β,7β-methylene-3-oxo-D-homo-17aα-pregna-4,16-diene-21-carboxylate (20 mg) was dissolved in 0.6 ml of methanol and 0.2 ml of 0.1N hydrochloric acid and kept at room temperature under argon for 10 minutes, a portion of the product crystallizing out. The mixture was poured into 20 ml of water. The precipitate was filtered and washed to neutrality with a small amount of water and dried. There was obtained 15 mg of crude product which, by gas chromatography was shown to consist exclusively of 6β,7β-methylene-3-oxo-D-homo-17aα-pregna-4,16-diene-21,17a-carbolactone.

EXAMPLE 5

A solution of 2.5 g of 6β,7β-methylene-3-oxo-D-homo-17aα-pregna-4,16-diene-21,17a-carbolactone and 1.9 g of 2,3-dichloro-5,6-dicyanobenzoquinone in 250 ml of dioxan was heated under reflux for 18 hours. The solution was treated with 250 ml of ethyl acetate and subsequently filtered through 100 g of aluminium oxide. The substance was totally eluted with an additional 300 ml of ethyl acetate. The filtrate was evaporated in vacuo and the residue was chromatographed on 250 g of silica gel. Elution with methylene chloride containing 2% acetone yielded 1.3 g of pure 6β,7β-methylene-3-oxo-D-homo-17aα-pregna-1,4,16-triene-21,17a-carbolactone, mp 261°–263° C.; $[\alpha]_D^{25}$ = –171° (c = 0.1, dioxan), $\epsilon_{243}$ = 12200.

EXAMPLE 6

By the method of Example 5, from 6α,7α-methylene-3-oxo-D-homo-17aα-pregna-4,16-diene-21,17a-carbolactone, there was obtained pure 6α,7α-methylene-3-oxo-D-homo-17aα-pregna-1,4,16-triene-21,17a-carbolactone, mp 232°–233° C.; $[\alpha]_D^{25}$ = +4° (c = 0.1, dioxan), $\epsilon_{244}$ = 13100.

The following Examples illustrate typical pharmaceutical preparations containing D-homosteroids of the present invention:

EXAMPLE 7

A tablet for oral administration can contain the following ingredients:

| | |
|---|---|
| Compound of formula I or pharmaceutically acceptable basic addition salt thereof | 25mg |
| Maize starch | 100mg |
| Lactose | 50mg |
| Polyvinylpyrrolidone | 15mg |
| Magnesium stearate | 2mg |

EXAMPLE 8

A capsule for oral administration can contain the following ingredients:

| | |
|---|---|
| Compound of formula I or pharmaceutically acceptable basic addition salt thereof | 25mg |
| Maize starch | 125mg |
| Lactose | 125mg |

We claim:
1. A compound of the formula

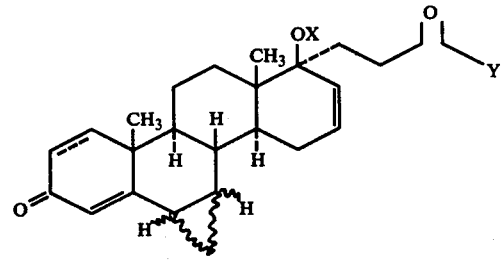

wherein X is hydrogen, Y is hydroxy or X and Y taken together denotes an oxygen to carbon bond and the dotted line in the 1,2-position of the A-ring together with the corresponding solid line denotes a single or double carbon to carbon bond or a pharmaceutically acceptable basic addition salt thereof when Y is hydroxy.

2. The compound of claim 1 wherein X is hydrogen, Y is hydroxy and the dotted line in the 1,2-position of the A-ring together with the corresponding solid line denotes a single carbon to carbon bond.

3. The compound of claim 2 which is 17a-hydroxy-6β,7β-methylene-3-oxo-D-homo-17aα-pregna-4,16-diene-21-carboxylic acid.

4. The compound of claim 1 wherein X and Y taken together denotes an oxygen to carbon bond and the dotted line in the 1,2-position of the A-ring together with the corresponding solid line denotes a single or double carbon to carbon bond.

5. The compound of claim 4 which is 6β,7β-methylene-3-oxo-D-homo-17aα-pregna-4,16-diene-21,17a-carbolactone.

6. The compound of claim 4 which is 6α,7α-methylene-3-oxo-D-homo-17aα-pregna-4,16-diene-21,17a-carbolactone.

* * * * *